(12) United States Patent
Moumene et al.

(10) Patent No.: US 7,156,876 B2
(45) Date of Patent: Jan. 2, 2007

(54) INTERVERTEBRAL MOTION DISC HAVING ARTICULATION AND SHOCK ABSORPTION

(75) Inventors: Missoum Moumene, West Newton, MA (US); John Riley Hawkins, Cumberland, RI (US)

(73) Assignee: Depuy Acromed, Inc., Raynham, MA (US)

( * ) Notice: Subject to any disclaimer, the term of this patent is extended or adjusted under 35 U.S.C. 154(b) by 36 days.

(21) Appl. No.: 10/681,473

(22) Filed: Oct. 8, 2003

(65) Prior Publication Data

US 2004/0073310 A1  Apr. 15, 2004

Related U.S. Application Data

(60) Provisional application No. 60/417,294, filed on Oct. 9, 2002.

(51) Int. Cl.
*A61F 2/44* (2006.01)
(52) U.S. Cl. .................................................. 623/17.13
(58) Field of Classification Search ............. 623/17.11, 623/17.12, 17.13, 17.14, 17.15, 17.16; 606/61
See application file for complete search history.

(56) References Cited

U.S. PATENT DOCUMENTS

| | | | | |
|---|---|---|---|---|
| 4,759,766 A | | 7/1988 | Buettner-Janz | |
| 4,759,769 A | * | 7/1988 | Hedman et al. | 623/17.13 |
| 4,911,718 A | * | 3/1990 | Lee et al. | 623/17.15 |
| 5,071,437 A | * | 12/1991 | Steffee | 623/17.16 |
| 5,314,477 A | | 5/1994 | Marnay | |
| 5,458,642 A | * | 10/1995 | Beer et al. | 623/17.13 |
| 5,507,816 A | | 4/1996 | Bullivant | |
| 5,534,030 A | * | 7/1996 | Navarro et al. | 623/17.15 |
| 5,674,296 A | * | 10/1997 | Bryan et al. | 623/17.16 |
| 5,676,701 A | | 10/1997 | Yuan | |
| 5,824,094 A | * | 10/1998 | Serhan et al. | 623/17.16 |
| 6,228,118 B1 | * | 5/2001 | Gordon | 623/17.14 |
| 6,368,350 B1 | | 4/2002 | Erickson | |
| 6,395,032 B1 | * | 5/2002 | Gauchet | 623/17.12 |
| 6,454,806 B1 | * | 9/2002 | Cohen et al. | 623/17.15 |
| 6,520,996 B1 | * | 2/2003 | Manasas et al. | 623/23.5 |
| 6,582,466 B1 | * | 6/2003 | Gauchet | 623/17.11 |
| 6,607,558 B1 | * | 8/2003 | Kuras | 623/17.16 |
| 6,726,720 B1 | * | 4/2004 | Ross et al. | 623/17.13 |
| 6,733,532 B1 | * | 5/2004 | Gauchet et al. | 623/17.12 |
| 6,749,635 B1 | * | 6/2004 | Bryan | 623/17.16 |
| 2001/0018614 A1 | * | 8/2001 | Bianchi | 623/16.11 |
| 2002/0035400 A1 | * | 3/2002 | Bryan et al. | 623/17.15 |
| 2003/0191534 A1 | | 10/2003 | Viart et al. | |
| 2003/0220691 A1 | * | 11/2003 | Songer et al. | 623/17.14 |

FOREIGN PATENT DOCUMENTS

FR  2 730 159  2/1995

* cited by examiner

*Primary Examiner*—Eduardo C. Robert
*Assistant Examiner*—Annette R. Reimers (57) ABSTRACT

A motion disc having an intermediate portion including a central articulating core component adapted to maintain the proper intervertebral spacing and a peripheral shock-absorbing component.

14 Claims, 5 Drawing Sheets

INTERVERTEBRAL MOTION DISC HAVING ARTICULATION AND SHOCK ABSORPTION

RELATED APPLICATIONS

This application claims priority from U.S. Provisional Application No. 60/417,294, by Moumene, entitled "Artificial Spinal Disc Replacement", filed Oct. 9, 2002. The entire teachings of the above applications are incorporated herein by reference.

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint. One proposed method of managing these problems is to remove the problematic disc and replace it with a prosthetic disc that allows for the natural motion between the adjacent vertebrae ("a motion disc").

U.S. Pat. No. 6,368,350 ("Erickson") discloses a three-piece motion disc providing two articulation surfaces. The disc comprises a first piece having a curved surface, a second piece having a flat surface, and an intermediate piece having a corresponding curved articulation surface and a corresponding flat articulation surface. Lastly, Erickson teaches that a variety of materials can be selected as materials of construction for the components of its device, including metals, polymers, and ceramics, and specifically teaches preferred combinations including metal-metal or metal-plastic combinations.

Erickson does not teach providing a shock-absorbing component in addition to the articulating component between the prosthetic endplates.

U.S. Pat. No. 5,676,701 ("Yuan") discloses, in one embodiment, a motion disc having a single articulation surface. This device includes a first component whose inner surface comprises a concave inner portion having a 360° circumference and a convex peripheral portion, and an opposing second component whose inner surface comprises a conforming convex inner portion and a convex peripheral portion. The convex/concave contours of the opposing inner portions forms a ball-and-socket design that allows unrestricted pivotal motion of the device, while the opposing convex peripheral contours allow flexion/extension bending motion in the range of about 20–30°.

However, Yuan does not teach providing a shock-absorbing component in addition to the articulating component between the prosthetic endplates.

U.S. Pat. No. 5,507,816 ("Bullivant") discloses a three-piece motion disc providing two articulation interfaces and comprises an upper piece having a flat lower surface, a middle spacer having a flat upper surface and a convex lower surface, and a lower piece having a concave upper surface. The articulating convex and concave surfaces form an articulating interface that allows pivotal motion, while the flat surfaces form a translation interface that allows translational motion.

Bullivant does not teach providing a shock-absorbing component in addition to the articulating component between the prosthetic endplates.

U.S. Pat. No. 4,759,766("Buttner-Janz") discloses a motion device comprising three components: an inferior endplate, a superior endplate, and a core having two articulation interfaces. Both the inferior and superior endplates are metal and have raised bosses with concave spherical surfaces in the center. The core is plastic and has convex surfaces on both the top and bottom which are surrounded by raised rims.

Buttner-Janz does not teach providing a shock-absorbing component in addition to the articulating component between the prosthetic endplates.

U.S. Pat. No. 5,314,477 ("Marnay") discloses a device having a single articulation interface and comprises three components: an inferior endplate, a superior endplate, and a plastic insert. The inferior endplate functions as a baseplate and has a sidewall forming an open ended channel for reception of the insert. The inner surface of the inferior endplate provides only stationary support for the insert and does not have a motion surface. Since the plastic insert is designed to be locked securely into place within the inferior endplate, the inferior surface of the insert is not a motion surface. The superior surface of the insert includes articulation surface for articulation with the superior endplate. The superior endplate has an inferior articulation surface that articulates with the superior motion surface of the plastic insert, and a superior surface designed for attachment to a vertebral endplate.

Marnay does not teach providing a shock-absorbing component in addition to the articulating component between the prosthetic endplates.

French Published Patent Application No. 2,730,159 ("Germain") discloses a motion disc in which the core member has one convex and concave surface. Germain further teaches that the radius of the upper curved surface (3$a$) of the core member is less than the radius of the lower curved surface (3$b$) of the core member.

Germain does not teach providing a shock-absorbing component in addition to the articulating component between the prosthetic endplates.

U.S. Pat. No. 5,824,094 ("Serhan") discloses a cushion-type motion disc wherein a rubber core is sandwiched between two metal prosthetic endplates. The rubber core provides a shock-absorbing effect and so mimics the natural response to axial load. However, the rubber core was found to experience high shear stresses in use.

In sum, the prior art does not disclose a motion device having two articulation interfaces that provides for both articulation and shock-absorption.

SUMMARY OF THE INVENTION

The present invention relates to a motion disc comprising opposing endplates and an intermediate portion comprising a central articulating core component and a peripheral shock-absorbing component.

In preferred embodiments, the central articulating core component is adapted to articulate with each of the opposing endplates and thereby maintain the proper intervertebral spacing and full range of motion. The surrounding shock-absorbing component provides the stiffness and shock-absorbing qualities of the natural disc in both flexion and torsion while centrally maintaining the core.

Therefore, in accordance with the present invention, there is provided a motion disc comprising:
a) a first prosthetic vertebral endplate comprising:
  i) an first outer surface adapted to mate with a first vertebral body,
  ii) an first inner surface comprising an first peripheral surface and a first articulation surface, iii) a body portion connecting the first inner and outer surfaces,
b) a second prosthetic vertebral endplate comprising:
   i) an second outer surface adapted to mate with a second vertebral body, and
   ii) an second inner surface comprising a second peripheral surface and a second articulation surface,
   iii) a body portion connecting the second inner and outer surfaces,
c) an articulating core member comprising:
   i) a first articulation surface adapted for articulation with the first articulation surface of the first endplate, and
   ii) a second articulation surface adapted for articulation with the first articulation surface of the second endplate, wherein the articulating core member is disposed between the prosthetic endplates and oriented to produce a first articulation interface between the first articulation surface of the first endplate and the first articulation surface of the core member, and a second articulation interface between the first articulation surface of the second endplate and the second articulation surface of the core member, and
d) a peripheral shock-absorbing component comprising:
   i) a first surface contacting the first peripheral surface of the first endplate, and
   ii) a second surface contacting the second peripheral surface of the second endplate.

DETAILED DESCRIPTION OF THE INVENTION

For the purposes of the present invention, "prosthetic vertebral endplate" broadly describes a component designed to substantially fit within an interverterbal space and mate with an opposing surface of one of the adjacent vertebral bodies. The "prosthetic vertebral endplate" includes all geometric configurations, including but not limited to substantially thin and substantially blocky configurations. Types of mating include, but are not limited to, penetrating the adjacent vertebral body, simply contacting the adjacent vertebral body, and providing fixation through a third component such as a fastener (such as a screw) that is received within or connected to the prosthetic vertebral endplate. Such fixation may occur upon a non-opposing surface of the adjacent vertebral body (such as the anterior wall of the vertebral body). The adjacent vertebral body may be prepared or unprepared so that the contacting surface thereof may include the cortical end endplate portion of the vertebral body or the internal cancellous portion of the vertebral body.

For the purposes of the present invention, a "substantially curved articulation interface" produces substantially pivotal motion during articulation. Examples of such substantially curved interfaces include but are not limited to hemipsherical interfaces having a radius of between about 10 mm and about 30 mm.

For the purposes of the present invention, both "slightly curved articulation interfaces" and "substantially flat articulation interfaces" produce substantially translational motion during articulation. Examples of such "slightly curved interfaces" include but are not limited to hemispherical interfaces having a radius of between about 40 mm and about 100 mm. For the purposes of the present invention, a "substantially flat articulation interface" is sufficiently flat so as to allow axial rotation of either mating component at any point along the interface.

Figure 1:
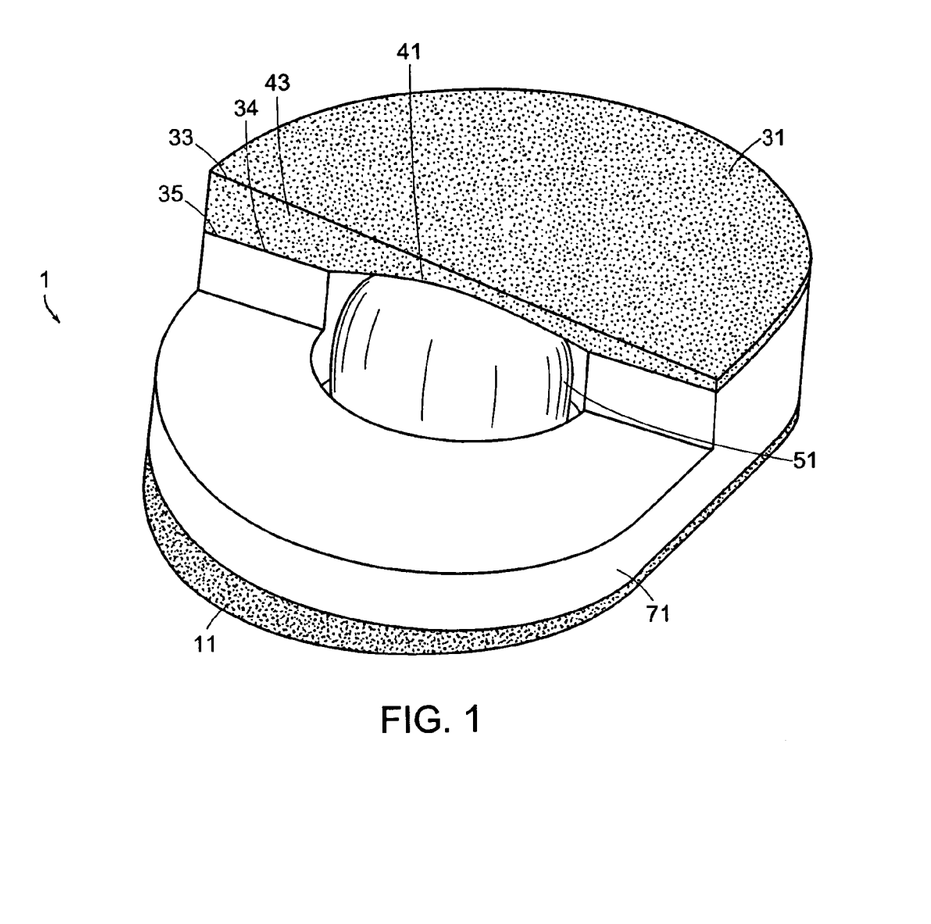
FIG. 1 discloses a partial cross-sectional view of an embodiment of the motion disc of the present invention.
Figure 2:
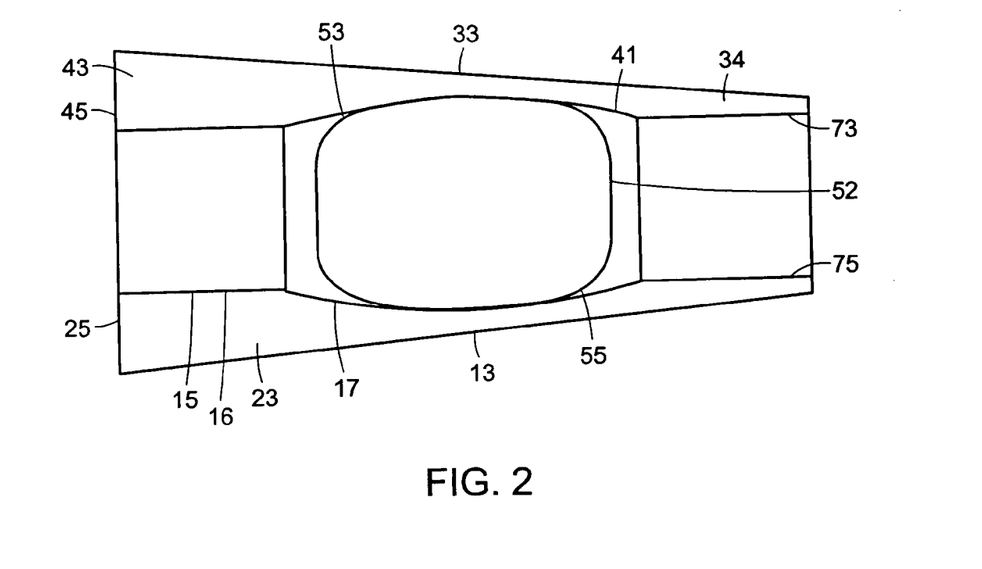
FIG. 2 discloses a full anterior-posterior cross-sectional view of an embodiment of the motion disc of the present invention.

Now referring to FIGS. 1 and 2, there is provided a motion disc 1 comprising:
a) a first prosthetic vertebral endplate 31 comprising:
   i) an outer surface 33 adapted to mate with a first vertebral body,
   ii) an inner surface 35 having an peripheral surface 34 thereon and a first articulation surface 41,
   iii) a body portion 43 connecting the inner and outer surfaces and defining a sidewall 45,
b) a second prosthetic vertebral endplate 11 comprising:
   i) an outer surface 13 adapted to mate with a second vertebral body, and
   ii) an inner surface 15 comprising a peripheral surface 16 and a first articulation surface 17,
   iii) a body portion 23 connecting the inner and outer surfaces and defining a sidewall 25,
c) an articulating core member 51 comprising:
   i) a first articulation surface 53 adapted for articulation with the first articulation surface of the first endplate, and
   ii) a second articulation surface 55 adapted for articulation with the first articulation surface of the second endplate,
c) a peripheral shock-absorbing component 71 comprising:
   i) a first surface 73 contacting the peripheral surface of the first endplate, and
   ii) a second surface 75 contacting the peripheral surface of the second endplate, wherein the core member is disposed within the channel and oriented therein to produce a first articulation interface between the first articulation surface of the first endplate and the first articulation surface of the core member, and a second articulation interface between the first articulation surface of the second endplate and the second articulation surface of the core member.

Generally, the device comprises four main components: an inferior endplate 11, a superior endplate 31, a centrally disposed articulating core member 51, and a peripheral shock absorber 71.

Each of the four main components of one preferred embodiment will now be described in more detail:

Now referring to FIGS. 1 and 2, in one embodiment, inferior endplate 11 has an inferior surface 13 designed to mate with a natural vertebral endplate, a superior surface 15 whose periphery is designed for tenacious attachment to the shock-absorbing member and whose central portion is designed for articulation with the core member, and a body portion 23 therebetween.

Preferably, the inferior (outer) surface 13 of this endplate is either flat, curved or domed to match the natural vertebral endplate. Alternatively, the geometry of the inferior surface can be designed so that it will match the shape of the patient's vertebral endplate after the vertebral endplate has been modified by an endplate-shaping instrument. In addition, the inferior surface of this endplate can further comprise features to promote and secure initial fixation and bony ingrowth including, but not limited to, spikes, keels, teeth, projections (such as dovetails), recesses (such as grooves) and porous coatings.

Superior (inner) surface 15 comprises a non-articulating peripheral portion 16 and a a highly polished substantially concave articulation surface 17 designed to mate with a corresponding substantially convex articulation surface disposed upon the core member. Preferably, substantially concave articulation surface 17 is further designed to conform to the corresponding concave articulation surface. In the preferred embodiment the articulation surface 17 is concave. However, the substantially curved articulation surface can also be convex if desired to mate with a corresponding substantially concave articulation surface (not shown) disposed upon the core member. Preferably, the substantially curved articulation surface 17 has been polished to a surface roughness Ra of no more than 100 nm.

Figure 3:
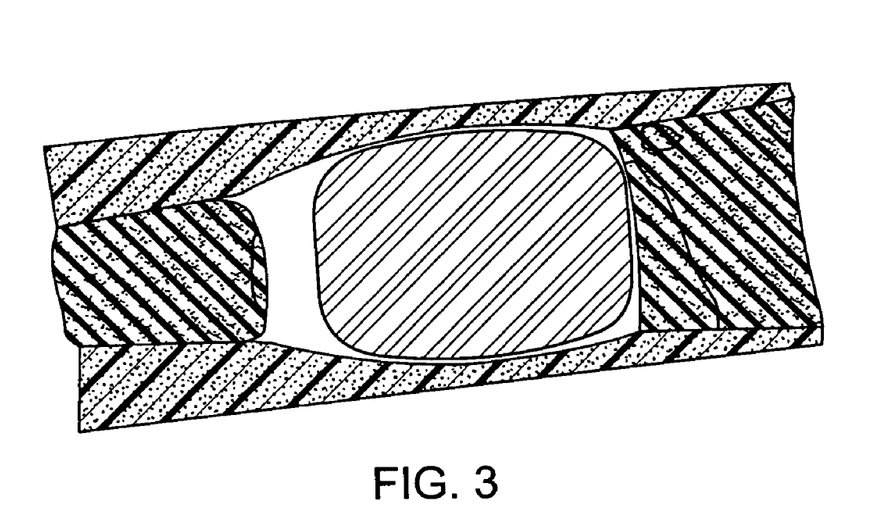
FIG. 3 discloses a cross-sectional view of the response of the device of FIG. 2 physiologic flexion.

Now referring to FIG. 3, superior endplate 31 has a superior outer surface 33 designed to mate with the vertebral endplate, an inferior inner surface 35 whose periphery is designed for tenacious attachment to the shock-absorbing member and whose central portion is designed for articulation with the core member, and a body portion 43 therebetween defining a sidewall.

Preferably, the superior outer surface 33 of this endplate is either flat, curved or domed to match the natural vertebral endplate. Alternatively, the geometry of the superior surface can be designed so that it will match the shape of the patient's vertebral endplate after the vertebral endplate has been modified by an endplate-shaping instrument. In addition, the superior surface of this endplate can further comprise features to promote secure initial fixation and bony ingrowth including, but not limited to, spikes, keels, teeth, projections (such as dovetails), recesses (such as grooves) and porous coatings.

Inferior (inner) surface 35 comprises a non-articulating peripheral portion 34 and a a highly polished substantially concave articulation surface 41 designed to mate with a corresponding substantially convex articulation surface disposed upon the core member. Preferably, substantially concave articulation surface 41 is further designed to conform to the corresponding convex articulation surface of the core. In the preferred embodiment the articulation surface 41 is concave. However, the substantially curved articulation surface can also be convex if desired to mate with a corresponding substantially concave articulation surface (not shown) disposed upon the core member. Preferably, the substantially curved articulation surface 41 has been polished to a surface roughness Ra of no more than 100 nm.

In the device shown in FIGS. 1 and 2, the body portion of each endplate is thicker in the anterior portion than in the posterior portion. This difference provides the implant with desirable lordosis. Preferably, the angle of lordosis provided by the implant is between 5 and 20 degrees. More preferably, the angle of lordosis provided by the implant matches that of an intact healthy disc for the given level of implantation. In other embodiments, the body portion of each endplate is equal in the posterior and anterior portions.

Still referring to FIGS. 1 and 2, the core member 51 comprises a body portion 52 forming a convex superior surface 53 that is designed to articulate with the bottom surface of the superior endplate and a convex inferior surface 55 that is designed to mate with the inferior endplate. In some preferred embodiments, the body portion has a substantially cylindrical body portion 52. Preferably, superior surface 53 is further designed to conform to the bottom surface 41 of the superior endplate. Also preferably, convex inferior surface 55 is designed to conform with a corresponding substantially curved upper surface of the inferior endplate. In some embodiments (not shown), one of the core articulation surfaces is substantially flat to provide substantially translational motion with a corresponding flat bottom surface of a corresponding endplate. However, in other embodiments, one of the core articulating surfaces is slightly curved to provide substantially translational motion with a corresponding curved surface of the corresponding endplate as well as soft resistance to extreme translational motion.

The substantially curved articulation surfaces of the core can be any shape designed for pivotal articulation, including hemispherical, hemicylindrical, hemi-ellipsoidal, and oblong. However, in preferred embodiments, the curved surface is hemi-spherical. In the preferred embodiments, the substantially curved articulation surfaces of the core are convex. However, the curved articulation surface can also be concave, if desired, to mate with a corresponding substantially convex articulation surface disposed upon an endplate.

The substantially curved articulation surfaces of the core may be modified to any slightly curved geometry that allows at least one degree of substantially translational motion, including a hemi-cylindrical shape.

Preferably, the radius of each of the upper and lower articulation surfaces of the core is between about 40 mm and about 100 mm, and the radius of the lower articulation surface is between about 10 mm and about 30 mm, more preferably between 40 mm and 80 mm. Below 40 mm, the depth of the curve requires adding significantly more material to the corresponding endplate, thereby increasing the height of the implant. Above 80 mm, the curve provides a less significant braking.

Preferably, the non-spherical curved articulation surfaces of the core are hemicylindrical surfaces, as such a surface that can articulate with a similar opposing hemicylindrical surface and in some embodiments provide conforming articulation. Also preferably, the curved dimension of the hemicylindrical surface is provided in the A-P direction (to provide a soft braking) while the linear dimension is provided in the medial-lateral direction. However, in other embodiments, the curved dimension of the hemicylindrical surface is provided in the medial-lateral direction, while the linear dimension is provided in the anterior-posterior direction.

Also preferably, the hemispherical surface is substantially curved and the curved, non-hemispherical surface is slightly curved.

The primary function of the shock-absorbing component is to provide axial and torsional stiffness and dampening. In some embodiments, the material of the shock-absorbing component is selected to provide a spring constant of between about 500 N/mm and 1000 N/mm. When the shock-absorbing component is so designed, it can absorb between about 5,000 N and 10,000 N of axial load.

In the embodiment of FIG. 1, the shock-absorbing component is tenaciously attached to the opposing endplates. The methods disclosed in Serhan, supra, are suitable for providing such attachment. The tenacious attachment mitigates wear concerns at this interface.

When the peripheral shock-absorber is tenaciously attached, the issue of assembling the core into the central space must be addressed. In some embodiments (not shown), at least one of the endplates of the device of FIG. 1 is modified with a window whose edges are threaded for threaded reception of threaded plug. In this case, the peripheral shock-absorb can be tenaciously attached to the endplates with the window open, the core can be inserted through the open window, and then the window can be closed with the threaded plug.

FIG. 3 discloses the response of the motion disc of the present invention to an anteriorly-located axial load. In this particular test, the overall height of the device was set at about 10 mm while the cross-sectional length was about 24 mm. In the test, the upper left hand corner of the device was subjected to a purely axial load such that the upper left hand corner was displaced by 2 mm. FIG. 3 discloses the displacement response of the device. Review of the FIG. 3 indicates that the greatest displacement occurs in the areas closer to the upper left hand corner of the device. Further review also reveals that the left hand portion of the shock-absorbing component is essentially reduced in height (to about 7 mm) while the right hand portion, while the right hand portion of the shock-absorbing component is essentially increased in height (to about 11 mm).

Also as shown in FIG. 3, the core component of the device responds to this anterior load by shifting posteriorly. This movement shifts the center of rotation of the motion device. Since it is known that the center of rotation of the natural intervertebral disc also responds to an anterior load by shifting posteriorly, the response of the device essentially mimics that of a natural intervertebral disc.

Figure 4:
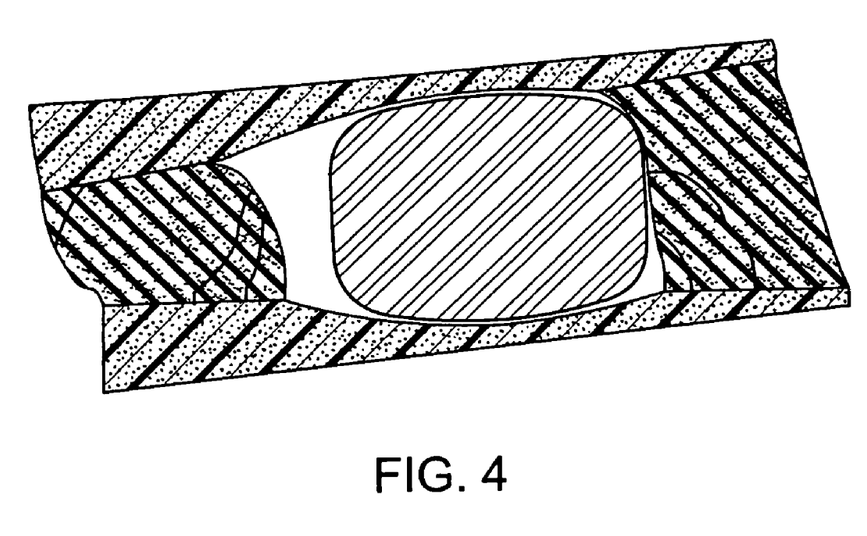
FIG. 4 discloses a cross-sectional view of the response of the device of FIG. 2 to physiologic flexion and compression.

FIG. 4 disclose the response of the motion disc of the present invention to not only the anteriorly-located axial load but also a physiologic compression load.

Figure 5A:
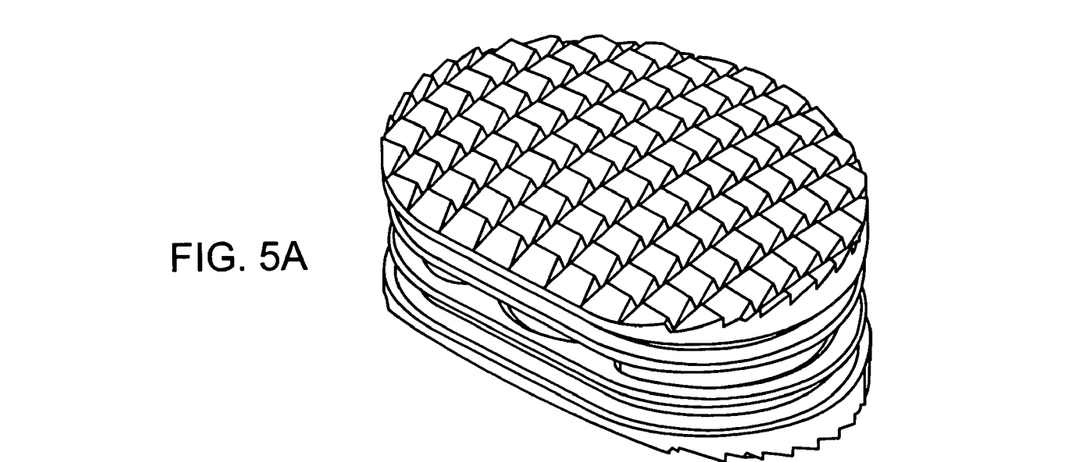
FIGS. 5a–5c disclose an embodiment of the present invention in which the peripheral shock-absorbing component is not tenaciously attached to the endplates.
Figure 5B:
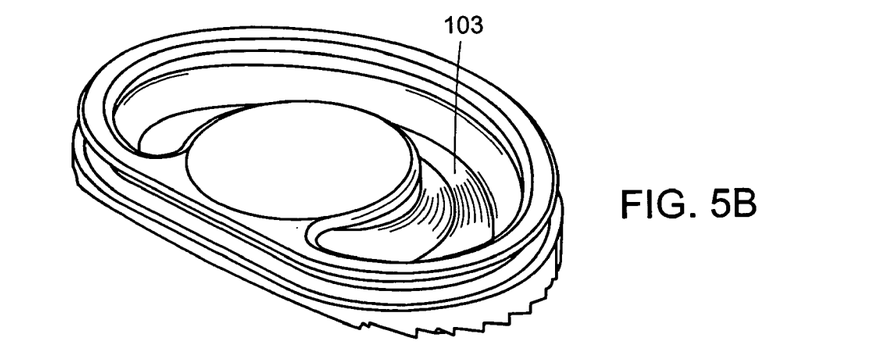
Figure 5C:
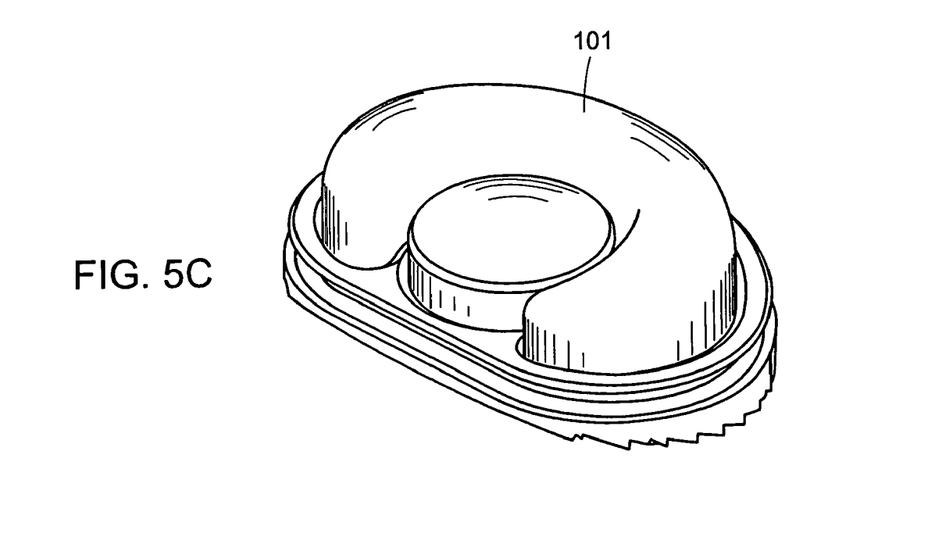

Now referring to FIGS. 5a–5c, in some embodiments, the shock-absorbing component 101 is not tenaciously attached to the opposing endplates, but rather is inserted into opposed channels 103 provided in the interior surfaces of the opposed endplates and adapted to closely receive the peripheral shock-absorber 101. This "soft" attachment mitigates concerns related to the shear stresses present at the interfaces of the endplates and the tenaciously-attached shock-absorber. Because each of the endplate, core and shock-absorbing components are free-standing, they can be assembled by the surgeon at the point of care.

The embodiment of FIG. 5a also discloses a toothed pattern upon the outer surfaces of each prosthetic endplate.

In some embodiments, the device further comprises a sheath adapted to at least partially enclose the articulation surfaces. This enclosure advantageously protects the articulation surface from unwanted exposure to the physiologic environment, thereby preventing intrusion of body fluids and debris, retaining any wear debris produced by the articulation (thereby preventing an immune response), and/or retaining any articulation fluid deliberately deposited upon the articulation surface. In some embodiments, the sheath material of construction is selected from the group consisting a fabric and an elastomer. In some embodiments, the sheath design is selected from the group consisting of a bag and a tube. In some embodiments, the sheath is adapted to essentially fully enclose the articulation surfaces.

In some embodiments, the device comprises at least two articulating core members. When two articulating core members are provided, the loading upon the device may be more evenly distributed.

In some embodiments, the device comprises at least two shock-absorbing components. When two shock-absorbing components are provided, the loading upon the device may be more evenly distributed.

In some embodiments, the disc further comprises a lubricant disposed upon the first and/or second articulation interface in order to reduce friction and wear at the interface.

In preferred embodiments, each of the inferior endplate, superior endplate, core member and shock-absorbing component is manufactured from a material that possesses the strength and high wear resistance desired for use as a motion disc component.

These components of the present invention may be made from any non-resorbable material appropriate for human surgical implantation, including but not limited to, surgically appropriate metals, and non-metallic materials, such as carbon fiber composites, polymers and ceramics.

In some embodiments, the core material is selected from the group consisting of polyethylene, PEEK, ceramic and metals. The shock-absorbing component is preferably a biocompatible material without carbon black. The prosthetic endplate material is preferably selected from the group consisting of metal and composite (such as PEEK/carbon fiber).

If a metal is chosen as the material of construction for a component, then the metal is preferably selected from the group consisting of titanium, titanium alloys (such as Ti—6Al—4V), chrome alloys (such as CrCo or Cr—Co—Mo) and stainless steel.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; and mixtures thereof.

If a ceramic is chosen as the material of construction for a component, then the ceramic is preferably selected from the group consisting of alumina, zirconia and mixtures thereof. It is preferred to select an alumina-zirconia ceramic, such as BIOLOX delta™, available from CeramTec of Plochingen, Germany. Depending on the material chosen, a smooth surface coating may be provided thereon to improve performance and reduce particulate wear debris.

In some embodiments, the core member is polyethylene. In others, it is a ceramic.

In some embodiments, the first endplate consists essentially of a metallic material, preferably a titanium alloy or a chrome-cobalt alloy. In some embodiments, the second endplate consists essentially of the same metallic material as the first plate. In some embodiments, the articulation surfaces of the endplates may be coated with a wear-resistant coating, such as diamond film, in order to reduce wear.

In some embodiments, the endplates are made of a stainless steel alloy, preferably BioDur$^R$ CCM Plus$^R$ Alloy available from Carpenter Specialty Alloys, Carpenter Technology Corporation of Wyomissing, Pa.; and the core member is made of polyethylene, preferably Marathon™, available from DePuy Orthopaedics of Warsaw, Ind. In some embodiments, the endplate articulation surfaces are coated with a sintered beadcoating, preferably Porocoat™, available from DePuy Orthopaedics of Warsaw, Ind.

In some embodiments, the endplates are made from a composite comprising carbon fiber. Composites comprising carbon fiber are advantageous in that they typically have a strength and stiffness that is superior to neat polymer materials such as a polyarylethyl ketone PAEK. In some embodiments, however, each endplate is made from a polymer composite such as a PEKK-carbon fiber composite.

Preferably, the composite comprising carbon fiber further comprises a polymer. Preferably, the polymer is a polyarylethyl ketone PAEK. More preferably, the PAEK is selected from the group consisting of polyetherether ketone PEEK, polyether ketone ketone PEKK and polyether ketone PEK. In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present as chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
  a) 40–99% (more preferably, 60–80 vol %) polyarylethyl ketone PAEK, and
  b) 1–60% (more preferably, 20–40 vol %) carbon fiber, wherein the polyarylethyl ketone PAEK is selected from the group consisting of polyetherether ketone PEEK, polyether ketone ketone PEKK and polyether ketone PEK.

In some embodiments, the composite consists essentially of PAEK and carbon fiber. More preferably, the composite comprises 60–80 wt % PAEK and 20–40 wt % carbon fiber. Still more preferably the composite comprises 65–75 wt % PAEK and 25–35 wt % carbon fiber.

Generally, the peripheral shock-absorber is made of an elastomer, and is preferably an elastomer as selected in U.S. Pat. No. 5,824,094 ("Serhan"), the specification of which is incorporated by reference in its entirety. In some embodiments the elastomeric shock-absorber is preferably made of a polyolefin rubber or carbon black reinforced polyolefin rubber. The hardness of the elastomeric shock-absorber is preferably 56–72 shore A durometer. The ultimate tensile strength of the shock-absorber is preferably greater than 1600 psi. The shock-absorber preferably has an ultimate elongation greater than 300% using the ASTM D412-87 testing method, and a tear resistance greater than 100 psi using the ASTM D624-86 testing method. Although the elastomeric shock-absorber is disclosed as being made of a polyolefin rubber, it can be made of any elastomeric material that simulates the characteristics of a natural disc.

Although the present invention has been described with reference to its preferred embodiments, those skillful in the art will recognize changes that may be made in form and structure which do not depart from the spirit of the invention.

We claim:

1. A motion disc comprising:
  a) a first prosthetic vertebral endplate comprising:
    i) an first outer surface having a porous coating thereon and adapted to mate with a first vertebral body,
    ii) an first inner surface comprising an first peripheral surface and a first articulation surface,
    iii) a body portion connecting the first inner and outer surfaces,
  b) a second prosthetic vertebral endplate comprising:
    i) an second outer surface having a porous coating thereon and adapted to mate with a second vertebral body, and
    ii) an second inner surface comprising a second peripheral surface and a second articulation surface,
    iii) a body portion connecting the second inner and outer surfaces,
  c) an articulating core member adapted to maintain intervertebral spacing and comprising:
    i) a first articulation surface adapted for articulation with the first articulation surface of the first endplate, and
    ii) a second articulation surface adapted for articulation with the first articulation surface of the second endplate,
  wherein the articulating core member is disposed between the prosthetic endplates and oriented to produce a first articulation interface between the first articulation surface of the first endplate and the first articulation surface of the core member, and a second articulation interface between the first articulation surface of the second endplate and the second articulation surface of the core member, and
  d) a peripheral shock-absorbing component comprising:
    i) a first surface contacting the first peripheral surface of the first endplate, and
    ii) a second surface contacting the second peripheral surface of the second endplate,
  wherein the core component is selected from the group consisting of polyethylene, PEEK, ceramic and metals, and
  wherein the shock-absorbing component comprises an elastomer, and
  wherein each peripheral surface of the shock-absorbing component is tenaciously attached to the respective inner surface of each endplate.

2. The disc of claim 1 wherein each of the first and second articulation surfaces of the core component is convex.

3. The disc of claim 1 wherein each endplate is made of a non-metallic material.

4. The disc of claim 1 wherein each endplate is made of a polymer composite material.

5. The disc of claim 1 wherein each endplate is made of a PEEK-carbon fiber composite material.

6. The disc of claim 1 wherein the body portion of each endplate comprises a posterior portion and an anterior portion, wherein the anterior portion is thicker than the posterior portion, thereby providing lordosis.

7. The disc of claim 6 wherein the lordosis produces an angle of between 5 and 20 degrees.

8. The disc of claim 1 wherein the body portion of each endplate comprises a posterior portion and an anterior portion, wherein the anterior portion is equal in thickness to the posterior portion.

9. The disc of claim 1 wherein the interior surface of each opposed endplate comprises a channel adapted to closely receive the peripheral shock-absorber.

10. The disc of claim 1 wherein the peripheral shock absorbing component comprises a posterior portion and an anterior portion, wherein the anterior portion is thicker than the posterior portion, thereby providing lordosis.

11. The disc of claim 1 further comprising a sheath adapted to at least partially enclose the articulation surfaces.

12. The disc of claim 1 further comprising:
e) a second articulating core member comprising:
   i) a first articulation surface adapted for articulation with the first articulation surface of the first endplate, and
   ii) a second articulation surface adapted for articulation with the first articulation surface of the second endplate,
wherein the second articulating core member is disposed between the prosthetic endplates and oriented to produce a third articulation interface between the first articulation surface of the first endplate and the first articulation surface of the second articulating core member, and a fourth articulation interface between the first articulation surface of the second endplate and the second articulation surface of the second articulating core member.

13. The disc of claim 1 further comprising:
e) a second peripheral shock-absorbing component comprising:
   i) a first surface contacting the first peripheral surface of the first endplate, and
   ii) a second surface contacting the second peripheral surface of the second endplate.

14. The disc of claim 1 further comprising:
e) a lubricant disposed upon the first articulation interface.

* * * * *